United States Patent [19]

Bodicky

[11] 4,354,495

[45] Oct. 19, 1982

[54] METHOD OF CONNECTING PLASTIC TUBE TO A PLASTIC PART

[75] Inventor: Raymond O. Bodicky, St. Louis, Mo.

[73] Assignee: Sherwood Medical Industries Inc., St. Louis, Mo.

[21] Appl. No.: 201,890

[22] Filed: Oct. 30, 1980

[51] Int. Cl.³ .................... A61M 25/00; B29C 17/02
[52] U.S. Cl. .................................. 128/348; 264/127;
264/138; 264/150; 264/159; 264/230; 264/274;
264/292; 264/322
[58] Field of Search ............... 264/230, 274, 292, 322,
264/127, 138, 150, 159; 128/214.4, 221, 348

[56] References Cited

U.S. PATENT DOCUMENTS

| 950,822 | 3/1910 | McElroy | 128/221 |
|---|---|---|---|
| 2,512,568 | 6/1950 | Saffir | 128/221 |
| 2,844,149 | 7/1958 | Gettig | 128/221 |
| 3,469,579 | 9/1969 | Hubert | 128/214.4 |
| 3,470,604 | 10/1969 | Zenick | 29/447 |
| 3,720,210 | 3/1973 | Diettrich | 128/214.4 |
| 3,721,231 | 3/1973 | Hubert | 128/348 |
| 3,861,972 | 1/1975 | Glover et al. | 156/86 |
| 4,155,966 | 5/1979 | Tschanz | 264/230 |

*Primary Examiner*—James B. Lowe
*Attorney, Agent, or Firm*—Stanley N. Garber; William R. O'Meara

[57] ABSTRACT

A method of connecting a plastic tube to a plastic hub is disclosed which includes preforming the tube by externally heating it in selected areas to cause outward bulging of the tube in those areas, applying an axial force on the tube to cause the bulges to compress axially while heated and molding the hub with the tube bulges in the mold.

24 Claims, 6 Drawing Figures

METHOD OF CONNECTING PLASTIC TUBE TO A PLASTIC PART

TECHNICAL FIELD

This invention relates to a method of connecting plastic parts together and more particularly to a method of connecting a plastic tube in fluid-tight connection with a plastic member.

BACKGROUND ART

Various methods have been used to connect plastic tubing in fluid-tight connection with other plastic parts, such as plastic fluid couplings or hubs used in medical devices such as catheters. Plastic tubes for intravenous catheter placement units or infusion sets, for example, are necessarily of small size since they are to be placed in a patient's vein for infusion purposes. The tube must be connected to a hub or other coupling that can be connected with a source of infusion liquid. The connection between the plastic tube and the hub must, of course, be fluid-tight as well as mechanically strong, and it must remain so throughout its use. Should the catheter tube become completely disconnected from its hub during use, it could move into the patient's vein. If a fluid leak occurs at the connection, the patient will receive less infusion liquid than intended and the liquid would flow outside the infusion system.

Because such tubing often has small inner and outer diameters, and must be made of a material which is substantially inert to the body, problems of obtaining a good mechanically strong connection, as well as a good fluid-tight connection with a plastic hub, which hub may be of a different material, have occurred. Also, certain tube materials may be of a type which do not chemically bond to the plastic material of the hub.

In some cases, sliding members or threaded coupling members are moved together to clamp a tube in place, and in some cases, a metal or plastic ferrule may be used. In U.S. Pat. No. 3,720,210, a tube of polytetrafluoroethylene, known under the trademark Teflon, is provided with an integral flange at one end and an additional outer tubular member or sleeve of a different plastic material, and the tube end and sleeve are insert molded in a hub member. However, such a method requires the use of the additional sleeve member. Also, in use, the tube may tend to rotate on its axis relative to the hub and this may result in the leaking of fluid from the system.

DISCLOSURE OF THE INVENTION

The present invention is directed to overcoming one or more of the problems set forth above and has for its object to provide an improved method of connecting a plastic tube to a plastic member to obtain a good fluid-tight connection therewith.

In accordance with one aspect of the present invention, a portion of a plastic tube is heated in a selected area from the exterior of the tube so that the plastic material expands outwardly due to the heat to form a bulge, the bulge is inserted into a mold, and a plastic member is molded about the bulge.

These, as well as other objects and advantages of the present invention, will become apparent from the following detailed description and accompanying drawing.

BRIEF OF DESCRIPTION OF DRAWING

BEST MODE FOR CARRYING OUT THE INVENTION

Figure 1:
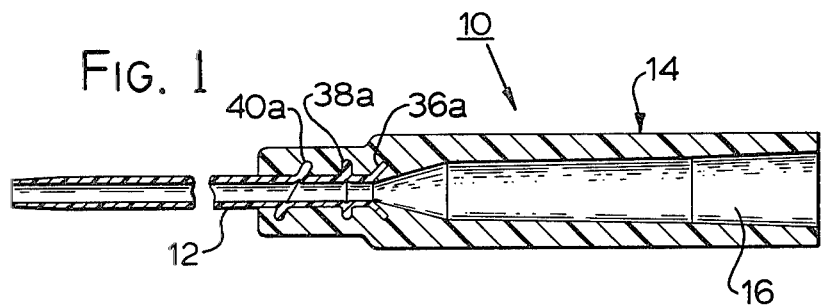
FIG. 1 is a side view in cross-section, of a finished catheter made in accordance with a preferred method of the present invention.

Referring now to the drawing and particularly to FIG. 1, there is shown for illustration a catheter 10 of the indwelling catheter type used, for example, in infusion sets. The catheter 10 includes a plastic tube 12 connected to a plastic member 14 shown as a fluid coupling device or hub. The catheter tube 12 is adapted to be inserted into the vein of the patient in a conventional manner. For example, a needle extending through the catheter and beyond the distal tip of the tube may be used to pierce the skin and vein and allow insertion of the tube. The needle is removed from the catheter 10 while maintaining the distal end of tube 12 in place in the vein. Catheter 10 may be taped to the arm of the patient. As shown in FIG. 1, the hub 14 has an internal or female luer connection, indicated at 16, for receiving and connecting a male luer connector (not shown) in fluid-tight connection to tubing of the infusion system for supplying infusion liquid, such as a saline solution, to the vein of the patient through tube 12.

The tube 12 is preferably of a plastic material which is substantially inert with respect to blood where it is intended to come in contact with blood. The tube 12 is therefore preferably of polytetrafluoroethylene, which material will be referred to hereinafter simply by the trademark "Teflon". Some other materials that may be used in some cases are polyvinyl chloride and urethane plastics. Also, in an indwelling catheter, the inner and outer diameter of the tube must be small since they are inserted into a vein. For example, catheters for this purpose may be from 14 to 22 gauge.

The hub 14 may be made of a variety of well known moldable plastics such as polyurethane, acrylics, polyethylene, polycarbonates and so forth.

In accordance with the present invention, the tube 12 is connected to hub 14 by a method which produces, in a simple and effective manner, a good mechanically strong connection between the tube and hub and one that is fluid-tight. In carrying out the method, a plastic tube of predetermined length is subjected to external heat in a selected area so that the plastic material swells in that area producing a bulge. That portion of the tube having the bulge is then inserted into the mold that is used to mold the hub. In this way, the tube portion having the bulge is embedded in the hub during the insert molding operation. A preferred method of making the catheter of FIG. 1 is illustrated in FIGS. 2 through 5.

Figure 2:
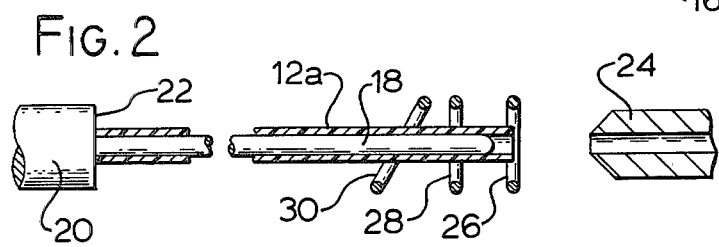
FIG. 2 is a side view of forming apparatus used in the manufacturing of the catheter of FIG. 1.

Referring to FIG. 2, a plastic tube 12a, preferably of extruded drawn-down Teflon, is shown inserted on a cylindrical rod 18 of a mandrel 20. The left end of the tube 12a engages a shoulder 22 of the mandrel while the right end portion of the tube extends a predetermined distance beyond the right end of rod 18. The rod 18 is in alignment with a retractable compression mandrel 24 which will be described hereinafter.

In the practice of the present invention, the material used in the plastic tube may be any plastic that is suitable for its intended use or purpose and which will bulge radially outwardly when sufficient heat is applied to the exterior of the tube. For example, extruded plastic tubing which is drawn-down when molten or soft (such as when it issues from an extruder) from a relatively large size to a relatively small size may be used. Drawn-down extruded tubing of Teflon, polyvinyl chloride or urethane, for example, may be employed in the disclosed process. Generally, plastic tubing that was drawn-down during its manufacture tends to bulge out or expand when a selected area is sufficiently heated, from the exterior, to its flowable state.

Figure 3:
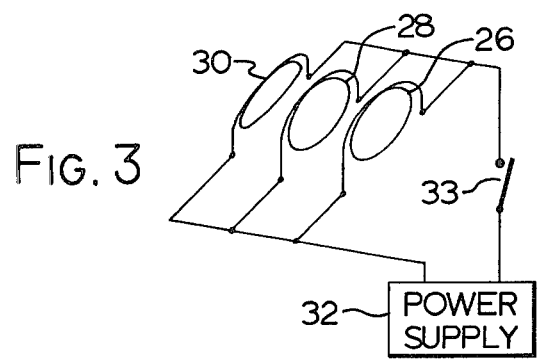
FIG. 3 is a schematic diagram of the heating circuit used in the forming apparatus of FIG. 2.

Three heating elements 26, 28 and 30 are shown as rings adjacent the exterior surface of the plastic tube 12a for causing swelling or bulging in selected areas of the tube 12a. FIG. 3 shows a schematic diagram of the heating element circuit. The heating rings 26, 28 and 30 are shown as looped wires, such as conventional heating element wires, for example, "Nichrome" wires, connected across a current source or power supply 32 through an on/off switch 33. As seen in FIG. 2, the rings 26 and 28 are axially spaced from each other and concentric with the tube 12a, while the ring 30 is slanted at an angle, e.g. 30°, to the right from a concentric position. The ring 26 is disposed adjacent the right end or tip of tube 12a.

Figure 4:
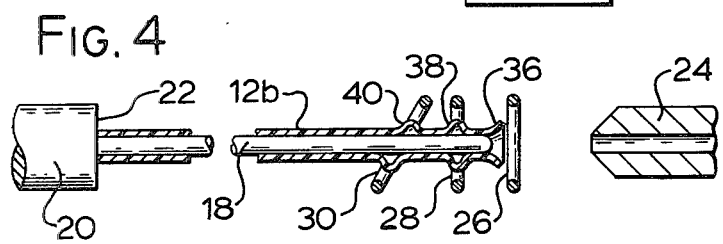
FIGS. 4 and 5 are side views, partly in section, of the forming apparatus of FIG. 2 and illustrating different stages in the manufacture of the catheter of FIG. 1.

When the switch 33 is closed, current flows through the heating rings 26, 28 and 30 causing portions of the plastic tube adjacent to the rings to soften and swell or bulge due to the applied heat as indicated in FIG. 4. The plastic tube, now indicated at 12b, is shown with heat formed bulges 36, 38 and 40. The bulge 36 is at the proximal end of the tube 12b and is in the form of a radially outwardly extending flare having a generally conical shape. The bulge 38 is in the form of a radially outwardly extending circular rib concentric with the tube. The bulge 40 is shown as a radially outwardly extending circular rib. The axis of the circle formed by the rib 40 is inclined to the longitudinal axis of the tube 12b so that this rib is eccentric with respect to the tube axis, the purpose of which will be discussed hereafter.

Figure 5:
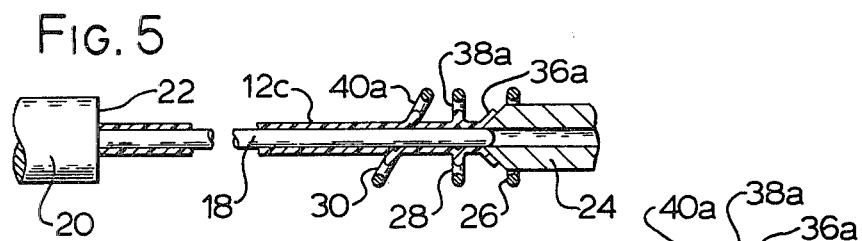
Figure 6:
FIG. 6 is a fragmentary side view of the proximal end of the tube of FIG. 5 after it is removed from the forming apparatus.

While the plastic material of tube 12b is softened by the heating rings in predetermined bulge areas, (heating element switch 33 may be moved to the open circuit position shown in FIG. 3) the compression mandrel 24 is moved axially into engagement with the inner walls of the flare 36 as seen in FIG. 5. Mandrel 24 applies an axial force to the tube 12b resulting in the inner walls of each of the bulges 38 and 40 moving together and the straightening of the inner sidewalls of flare 36. As shown in FIG. 5, the plastic tube, is now indicated as tube 12c, and the bulges are now shown as flare 36a, and ribs 38a and 40a. The tube 12c is cooled to the hardened state in its preformed condition of FIG. 5, and removed from the mandrel 20 after the compression mandrel 24 has been retracted or moved away from the tube. FIG. 6 shows the right end portion of tube 12c. Because of the axial compression step, the ribs 38a and 40a are of solid plastic and are more rigid and stronger than they were in their condition as ribs 38 and 40 in FIG. 4.

Next, the preformed tube 12c and the hub 14 are connected together by insert molding operations. The proximal end portion of tube 12c is disposed in the mold (not shown) in which hub 14 is molded so that the plastic tube material flows over the proximal end portion of the tube including the bulges 36a, 38a and 40a and with the hub material flowing distally beyond the bulge 40a. The material of hub 14 also flows partially under the flare 36a to embed the sidewalls of the flare in the hub material as apparent from FIG. 1. After cooling and hardening, the hub with the tube attached are removed from the mold. The distal end of the tube may then be tapered, as shown, in any conventional manner, for example, by grinding. The tapered distal end facilitates penetration of the skin and blood vessel.

It has been found that when catheters are made in accordance with the method described above, and even when the tube 12 as seen FIG. 1 is made of Teflon and of a small gauge, the tube connection with the hub is especially strong and will not leak fluid when in normal use. The flare 36a, as well as the ribs 38a and 40a, increase the path that would have to be taken by a fluid leaking from the hub 14 between the outer surface of the tube 12 and the hub. All three axially spaced bulges 36a, 38a and 40a, of course, oppose any axial or longitudinal forces tending to effect separation of the tube 12 from the hub 14. Also, since the circular rib 40a is angled or is eccentric with respect to the tube 12, that is, the axis of the circle defined by the outer surface of rib 40a is angularly offset from the longitudinal axis of tube 12, any forces tending to rotate the tube 12 on its longitudinal axis would be opposed by hub material entirely around the rib 40a. Since rib 40a would produce a relatively high resistance to rotation, substantially greater than concentric rib 38a, there is less chance of a fluid leakage paths being created by inadvertent forces on the tube 12 during use. Also, the described process is relatively simple and economic to perform.

While the heating elements are shown as rings 26, 28 and 30, they may take on various other configurations and preform the tube so that bulges of different configurations from those of 36a, 38a and 40a may be formed. For example, the bulges may be in the form of bubbles, longitudinal ribs at an angle to the tube axis, etc. In some cases depending upon size of parts a single bulge, preferably an eccentric bulge, such as bulge 40a, may be employed alone or with a flare, such as flare 36a. Preferably, at least two axially spaced bulges are preformed. While an indwelling catheter has been described, the process of the present invention may be used to make other devices where a plastic tube is to be connected to a plastic member.

The plastic member or hub 14 may be of various shapes and for various purposes. Instead of the hub shown, a hub may be used that is molded to provide a male coupling surface, threaded coupling surface, etc.

As various changes could be made in the above construction and method of making or process without departing from the scope of the invention, it is intended that all matter contained in the above description and process are shown in the accompanying drawing shall be interpreted as illustrative and not in a limiting sense.

I claim:

1. An indwelling catheter comprising a plastic tube having at least one generally annular bulge with an axis at an angle to the longitudinal axis of said tube formed by heating an annular area around an end portion of the tube but spaced from both ends of the tube to form a generally annular bulge with an axis at an angle to the longitudinal axis, and while the bulge is heat-softened moving inner facing walls of the bulge together, and a plastic hub having one end portion molded about said end portion of said tube including the bulge with the inner facing walls thereof together whereby any forces tending to rotate the tube about the longitudinal axis are opposed by increased resistance to such rotation as a result of the axis of said bulge being at an angle to the longitudinal axis, said hub having passage means in fluid communication with said tube.

2. The catheter of claim 1 wherein said tube has a flared end embedded in said plastic hub.

3. A method of connecting a plastic tube in fluid-tight connection with a plastic member comprising the steps of providing a tube of a plastic which when sufficiently heated in a selected area from the exterior side of the tube expands radially outwardly in that area to form a bulge on the tube, heating predetermined areas of the tube sufficiently from the exterior side thereof to form an outwardly extending bulge on the tube having axially spaced inner facing walls, applying a force on the tube with the walls in heat-softened condition to move the walls toward each other, and thereafter molding a plastic member about a portion of the tube which includes the bulge.

4. The method of claim 3 wherein the bulge is formed axially spaced from both ends of the tube and the step of applying a force includes moving the walls of the bulge together while the plastic of the bulge is soft, and thereafter cooling the bulge to a hardened state with the walls together.

5. The method of claim 3 wherein further including the step of heating the proximal end of the tube to produce a generally radially outwardly flaring end flare, and said molding step includes molding the plastic member also about the flare.

6. The method of claim 5 wherein said flare is formed while the tube is on a mandrel rod, and further including the step of moving a compression member against the flare while the flare is soft to reshape the flare.

7. The method of claim 6 wherein the step of moving the compression member against the flare includes effecting an axial compression of the bulge moving the facing walls of the bulge together.

8. The method of claim 3 wherein said step of heating includes positioning the tube on a rod and applying heat to the exterior surface of the predetermined areas to soften them while on the rod and form the bulge, and wherein pressure is applied to the axial end of the tube while on the rod and while the plastic of the bulge is soft to axially compress the bulge and move the facing walls thereof together.

9. The method of claim 3 or 8 wherein said heating step includes forming said bulge in the form of a generally annular rib around the tube spaced from both ends of the tube.

10. The method of claim 9 wherein said rib is formed so that the axis of the rib is at an angle to the longitudinal axis of the tube.

11. The method of claim 8 or 10 wherein said heating step includes forming a second generally annular rib around the tube and said step of applying a force includes moving inner facing walls of said second rib together.

12. The method of claim 11 wherein said second rib is concentric with the longitudinal axis of the tube.

13. The method of claim 9 wherein said step of heating includes surrounding at least a portion of the tube with an electric heating wire and connecting the wire to a source of current.

14. The method of claim 3 wherein said tube is produced by a method including drawing down molten plastic tubing of relatively large diameter to tubing of relatively small diameter and severing a portion of the drawn-down tubing to produce said tube of plastic.

15. The method of claim 3 or 14 wherein the plastic of said tube comprises polytetrafluoroethylene.

16. The method of claim 3, 4 or 8 wherein the gauge of the tube is within the size range of 14 to 22 gauge and the plastic materials of said tube and said member are different.

17. The method of making a medical device having a plastic tube connected in fluid-tight connection with a plastic hub comprising the steps of providing a plastic tube of predetermined length which when heated sufficiently in selected areas from the exterior side of the tube expands radially outwardly in that area to form a bulge, heating predetermined areas of a proximal end portion of the plastic tube sufficiently from the exterior side thereof to form a radially outwardly extending generally annular bulge thereon with the axis of the bulge at an angle to the longitudinal axis of the tube, cooling the tube sufficiently to harden the bulge, inserting the end portion of the plastic tube including the bulge into a hub mold, filling the mold with a plastic material to mold a hub with the plastic material about the bulge, cooling the plastic material of the hub and removing the hub from the mold with the tube bulge embedded in the hub.

18. The method of claim 17 including providing a mandrel having a rod, inserting the tube onto the rod before said heating step and performing said heating step while the tube is on said rod, and applying an axial compressive force on the tube after the bulge is formed and while the tube is on the rod and with the plastic of the bulge molten to move opposed inner walls of the bulge together.

19. The method of claim 17 or 18 wherein electric heating wire is used to effect the heating of the predetermined areas.

20. The method of claim 17 wherein the heating step includes forming an outwardly flaring flare at the proximal end of the tube in addition to said bulge.

21. The method of claim 4 or 17 further including the step of heat forming a second bulge at the proximal end of the tube spaced from the first named bulge.

22. The method of claim 20 wherein the step of applying an axial compressive force includes moving a compression mandrel against the flare while the plastic of the flare is molten to reshape the flare and move the inner facing walls of the bulge together.

23. The method of claim 17 wherein the plastic material of the hub is different from the plastic of the tube and the hub is formed with a passage communicating with the tube and has a means for coupling another member to the hub.

24. The method of claim 17 or 23 wherein the plastic of the tube comprises polytetrafluoroethylene.

* * * * *